US012751909B2

(12) United States Patent
Okishima et al.

(10) Patent No.: US 12,751,909 B2
(45) Date of Patent: Oct. 6, 2026

(54) COSMETIC PREPARATION

(71) Applicant: Shiseido Company, Ltd., Tokyo (JP)

(72) Inventors: Anna Okishima, Tokyo (JP); Mika Yoshimura, Tokyo (JP); Takashi Oka, Tokyo (JP); Hiroko Shimizu, Tokyo (JP)

(73) Assignee: Shiseido Company, Ltd., Tokyo (JP)

(*) Notice: Subject to any disclaimer, the term of this patent is extended or adjusted under 35 U.S.C. 154(b) by 556 days.

(21) Appl. No.: 18/271,521

(22) PCT Filed: Jan. 28, 2022

(86) PCT No.: PCT/JP2022/003408

§ 371 (c)(1),
(2) Date: Jul. 10, 2023

(87) PCT Pub. No.: WO2022/172790

PCT Pub. Date: Aug. 18, 2022

(65) Prior Publication Data

US 2024/0065962 A1 Feb. 29, 2024

(30) Foreign Application Priority Data

Feb. 10, 2021 (JP) ................................ 2021-020150

(51) Int. Cl.

| | |
|---|---|
| ***A61K 8/73*** | (2006.01) |
| ***A61K 8/19*** | (2006.01) |
| ***A61Q 5/00*** | (2006.01) |
| ***A61Q 19/00*** | (2006.01) |

(52) U.S. Cl.

CPC ................ *A61K 8/735* (2013.01); *A61K 8/19* (2013.01); *A61Q 5/00* (2013.01); *A61Q 19/00* (2013.01); *A61K 2800/51* (2013.01); *A61K 2800/546* (2013.01); *A61K 2800/884* (2013.01)

(58) Field of Classification Search

CPC ...... A61K 8/735; A61K 8/19; A61K 2800/51; A61K 2800/546; A61K 2800/884; A61Q 5/00; A61Q 19/00

USPC ........................................................... 514/62

See application file for complete search history.

(56) References Cited

U.S. PATENT DOCUMENTS

| | | | | |
|---|---|---|---|---|
| 10,588,924 | B1 | 3/2020 | Wootten | |
| 2015/0320915 | A1* | 11/2015 | Schmidt | A61F 2/0077 514/779 |
| 2021/0290819 | A1 | 9/2021 | Jang et al. | |
| 2022/0273545 | A1 | 9/2022 | Oka et al. | |

FOREIGN PATENT DOCUMENTS

| | | | |
|---|---|---|---|
| CN | 111297726 | A | 6/2020 |
| JP | 2010-150151 | A | 7/2010 |
| WO | WO-2018/182003 | A1 | 10/2018 |
| WO | WO-2020/013580 | A1 | 1/2020 |
| WO | WO-2021/033725 | A1 | 8/2020 |

OTHER PUBLICATIONS

Avon Perfectwear Extralasting Foundation, ingredients list, Mar. 17, 2011, CosDNA, 2 pages, https://www.cosdna.com/eng/cosmetic_0da049870.html.

Mintel GNPD [Online], "Illuminare Brightening Hand Serum," ID 1215073, Del Laboratories, Nov. 2009, 4 pages.

* cited by examiner

*Primary Examiner* — Yih-Horng Shiao

(74) *Attorney, Agent, or Firm* — Foley & Lardner LLP

(57) ABSTRACT

To provide a cosmetic whose moisture-retaining property can be sufficiently secured even in cases where the cosmetic uses a hyaluronic acid compacted by neutralization of carboxyl groups of hyaluronic acid using a salt.

A cosmetic of the present disclosure comprises a first agent containing at least one salt selected from the group consisting of an inorganic salt and an organic acid salt, and hyaluronic acid; and a second agent for swelling the hyaluronic acid, the second agent containing a chelating agent.

7 Claims, 9 Drawing Sheets

COSMETIC PREPARATION

CROSS-REFERENCE TO RELATED APPLICATIONS

This application is the U.S. National Stage of PCT/JP2022/003408, filed Jan. 28, 2022, which claims priority to JP 2021-020150, filed Feb. 10, 2021.

FIELD

The present disclosure relates to a cosmetic.

BACKGROUND

For the purpose of, for example, moisturization of the skin, hyaluronic acid, which has a moisturizing function, has been utilized in the fields of cosmetics and the like.

PTL 1 discloses a cosmetic comprising a hyaluronic acid-supported nanoparticle in which hyaluronic acid is supported in/on at least one of the inside or the surface of a nanoparticle formed of polylactic acid, polyglycolic acid, or a lactic acid-glycolic acid copolymer.

PTL 2 discloses an external preparation for the skin, comprising a composite nanoparticle containing: (A) hyaluronic acid; and (B) a zwitterionic compound; wherein the particle diameter is 100 nm or less.

PTL 3, which is unpublished, discloses a cosmetic comprising: an aqueous medium; and hyaluronic acid particles dispersed in the aqueous medium; wherein the average particle diameter of the hyaluronic acid particles is 200 nm or less.

CITATION LIST

Patent Literature

[PTL 1] Japanese Unexamined Patent Publication (Kokai) No. 2010-150151
[PTL 2] WO 2018/182003
[PTL 3] PCT/JP2020/031318

SUMMARY

Technical Problem

Hyaluronic acid has a negative charge due to the presence of carboxyl groups. Due to the electrostatic repulsion based on this negative charge, hyaluronic acid is generally in the form of spread filaments.

Compacted hyaluronic acids, such as those described in PTLs 1 and 2, are more likely to stay in grooves, pores, and the like of the skin compared to hyaluronic acids in the form of spread filaments. However, since the content ratio of hyaluronic acid in the particles described in PTL 1 is as low as about 3% by mass, and the content ratio of hyaluronic acid in the particles described in PTL 2 is only 50% by mass or less, there have been cases where a sufficient moisture-retaining property could not be secured.

As described in PTL 3, the present applicants, as researchers, discovered that the electrostatic shielding effect of an electrolyte such as sodium chloride can be utilized to apparently neutralize the carboxyl-derived negative charge of hyaluronic acid, to achieve dominance of hydrogen bonds, which have an attracting action, based on hydroxyl groups and the like in the hyaluronic acid, to thereby suppress spreading of the hyaluronic acid and enable compaction of the hyaluronic acid.

However, in cases where hyaluronic acid is compacted by using the technique described in PTL 3, the neutralization of carboxyl groups of the hyaluronic acid by the electrolyte such as sodium chloride may lead to a decrease in the amount of held water (the amount of hydration), so that the moisture-retaining property of hyaluronic acid itself cannot be sufficiently secured in some cases.

In view of this, a main object of the present disclosure is to provide a cosmetic whose moisture-retaining property can be sufficiently secured even in cases where the cosmetic uses a hyaluronic acid compacted by neutralization of carboxyl groups of hyaluronic acid using a salt.

Solution to Problem

<Aspect 1>

A cosmetic comprising:

a first agent containing:

at least one salt selected from the group consisting of an inorganic salt and an organic acid salt; and hyaluronic acid; and a second agent for swelling the hyaluronic acid, the second agent containing:

a chelating agent.

<Aspect 2>

The cosmetic according to aspect 1, wherein the volume of the hyaluronic acid in the first agent increases by application of the second agent to the first agent.

<Aspect 3>

The cosmetic according to aspect 1 or 2, wherein the hyaluronic acid is contained at 0.005% by mass or more with respect to the total amount of the first agent.

<Aspect 4>

The cosmetic according to any one of aspects 1 to 3, wherein a cation constituting the salt is a metal ion.

<Aspect 5>

The cosmetic according to any one of aspects 1 to 4, wherein the chelating agent is at least one selected from the group consisting of ethylenediaminetetraacetic acid, disodium ethylenediaminetetraacetate, trisodium ethylenediaminetetraacetate, nitrilotriacetic acid, sodium nitrilotriacetate, ammonium nitrilotriacetate, hydroxyethylethylenediaminetriacetic acid, sodium hydroxyethylethylenediaminetriacetate, pentetic acid, pentasodium pentetate, triethylenetetramine hexaacetic acid, sodium triethylenetetramine hexaacetate, imidisuccinic acid, tetrasodium imidisuccinate, ethylenediaminedisuccinic acid, trisodium ethylenediamine disuccinate, hydroxyethyliminodiacetic acid, disodium hydroxyethyliminodiacetate, iminodisuccinic acid, tetrasodium iminodisuccinate, triethylenetetramine hexaacetic acid, sodium triethylenetetramine hexaacetate, methylglycine diacetic acid, trisodium methylglycine diacetate, hydroxyiminodisuccinic acid, tetrasodium hydroxyiminodisuccinate, L-aspartic acid diacetic acid, tetrasodium L-aspartate diacetate, glutamic acid diacetic acid, tetrasodium glutamate diacetate, propanediaminetetraacetic acid, diammonium ethylenediaminetetraacetate, 1,3-diamino-2-hydroxypropane-tetraacetic acid, 1,3-diamino-2-hydroxypropane-tetraacetic acid, N,N-bis(2-hydroxyethyl)glycine, glycol ether diamine tetraacetic acid, dicarboxymethyl glutamic acid, tetrasodium dicarboxymethyl glutamate, diethylenetriaminepentaacetic acid, hexametaphosphoric acid, sodium hexametaphosphate, nitrilotris(methylenephosphonic acid), potassium nitrilotris(methylenephosphonate), 2-phosphonobutane-1,2,4-tricarboxylic acid, ethylenediaminetetramethylene phosphonic acid, pentasodium ethylenediaminetetramethylene phosphonate, phytic acid, and citric acid.

<Aspect 6>

The cosmetic according to any one of aspects 1 to 5, wherein the weight average molecular weight of the hyaluronic acid is 10,000,000 or less.

<Aspect 7>

A cosmetic method using the cosmetic according to any one of aspects 1 to 6, the method comprising:

applying the first agent to a body surface or body hair; and then applying the second agent to the application area of the first agent.

Advantageous Effects of Invention

The present disclosure can provide a cosmetic whose moisture-retaining property can be sufficiently secured even in cases where hyaluronic acid compacted by neutralization of carboxyl groups using a salt is used.

DESCRIPTION OF EMBODIMENTS

Figure 1:
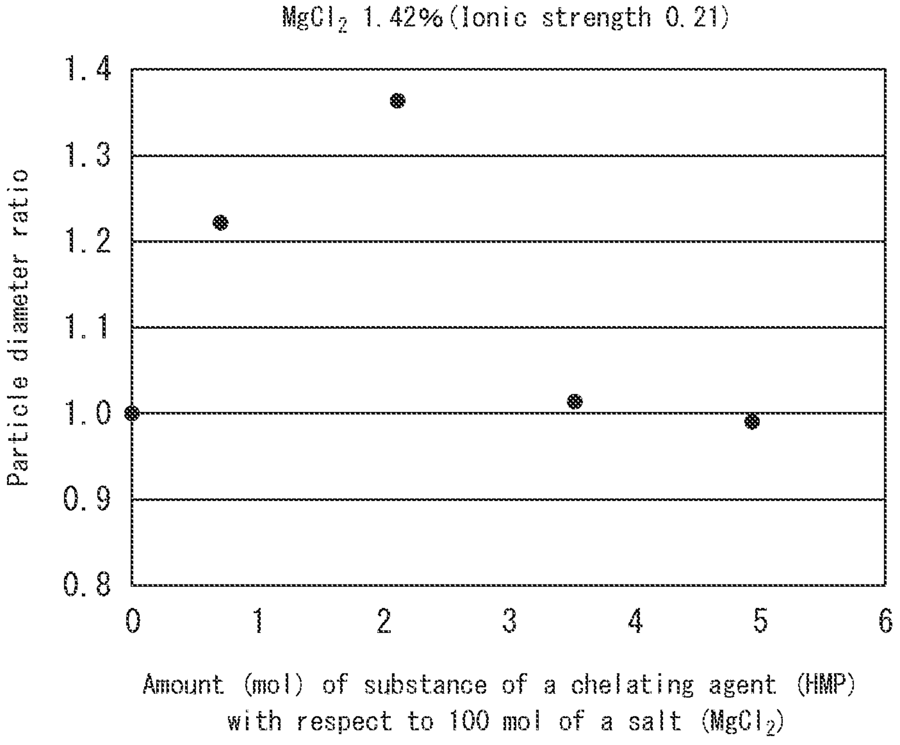
FIG. 1 is a graph related to the amount of substance (mol) of a chelating agent (HMP) with respect to 100 mol of a salt ($MgCl_2$), and the swelling property of a compacted hyaluronic acid.

Hereinafter, embodiments of the present disclosure are described in detail. The present disclosure is not limited to the following embodiments, and may be variously modified and practiced within the scope of the present invention.

The cosmetic of the present disclosure comprises:

a first agent containing:

at least one salt selected from the group consisting of an inorganic salt and an organic acid salt; and hyaluronic acid; and a second agent for swelling the hyaluronic acid, the second agent containing:

a chelating agent.

Although the present invention is not limited by the principle, the action principle that makes the cosmetic of the present disclosure capable of securing a sufficient moisture-retaining property even in cases where the cosmetic uses a hyaluronic acid compacted by neutralization of carboxyl groups of hyaluronic acid using a salt is thought to be as follows. Here, "compaction" in the present disclosure means that hyaluronic acid is shrunk compared to one molecule of hyaluronic acid, or compared to a structure in a state where a plurality of hyaluronic acid molecules are tangled together, the molecule or structure being in a state without addition of any salt. Typically, one molecule of hyaluronic acid, or a structure in a state where a plurality of hyaluronic acid molecules are tangled together, can be said to be shrunk in cases where a salt is contained together with the hyaluronic acid.

Hyaluronic acid generally has a negative charge due to the presence of carboxyl groups. Due to the electrostatic repulsion based on this negative charge, the molecule of hyaluronic acid was likely to be, for example, in the form of a spread filament, so that the molecule tended not to be compacted. Therefore, compaction of a structure of a hyaluronic acid molecule(s) by shrinkage required, as in the cases of PTLs 1 and 2, a nanoscale support material capable of supporting the hyaluronic acid molecule(s). As a result, the content ratio of hyaluronic acid in the compacted structure has been limited.

In contrast, according to the technique of PTL 3, the electrostatic shielding effect by an electrolyte such as sodium chloride can be utilized to apparently neutralize the negative charge of hyaluronic acid. As a result, dominance of hydrogen bonds can be achieved to suppress spreading of the hyaluronic acid molecule(s), so that compaction of even a hyaluronic acid molecule(s) alone is possible. Since the compacted structure of hyaluronic acid prepared by the technique of PTL 3 can be obtained without using the support material described above, the content ratio of hyaluronic acid in the structure can be theoretically 100% by mass.

However, in cases where a cosmetic containing a compacted structure of hyaluronic acid prepared in such a manner is applied to the skin or body hair, carboxyl groups of the hyaluronic acid continue to be neutralized by the electrolyte such as sodium chloride (for example, metal ions such as sodium ions). It is therefore thought that the carboxyl groups cannot sufficiently exert their ability to hold water (hydration capacity).

On the other hand, the cosmetic of the present disclosure comprises a second agent containing a chelating agent. Since the second agent is capable of capturing components that neutralize the negative charge of carboxyl groups (for example, metal ions such as sodium ions), it is thought that application of the second agent containing a chelating agent, after application of hyaluronic acid compacted using a salt to the skin or body hair, enables capturing of cations such as sodium ions that have been neutralizing carboxyl groups. It is thought that, as a result, the carboxyl groups of the hyaluronic acid can sufficiently exert their ability to hold water (hydration capacity), to provide a favorable moisture-retaining property for the skin or body hair.

Figure 2:
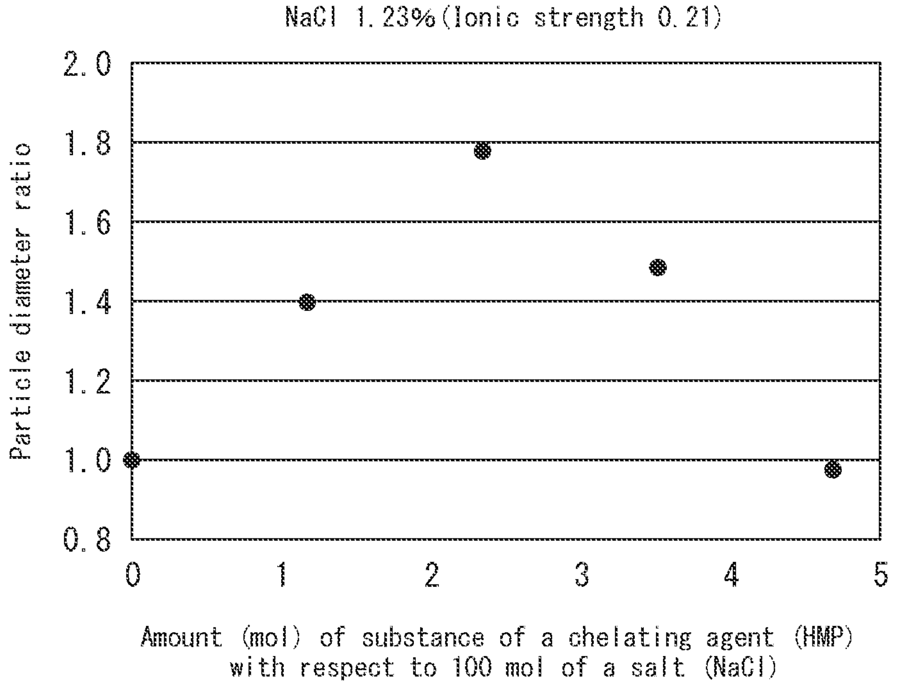
FIG. 2 is a graph related to the amount of substance (mol) of a chelating agent (HMP) with respect to 100 mol of a salt (NaCl), and the swelling property of a compacted hyaluronic acid.

The ability of the second agent containing a chelating agent to capture cations such as sodium ions that have been neutralizing carboxyl groups can be indirectly confirmed from, for example, FIGS. 1 and 2. Inclusion of a chelating agent in a solution containing hyaluronic acid compacted using a salt caused swelling of the compacted hyaluronic acid. This is thought to be due to the fact that the inclusion of the chelating agent caused capture of cations such as sodium ions, to decrease the electrostatic shielding effect, resulting in the occurrence of such a swelling phenomenon.

Since the chelating agent itself contains a metal ion, the hyaluronic acid can be compacted again as the amount of the chelating agent increases. The optimal amount of the chelating agent varies depending on, for example, the type of the chelating agent. As long as the second agent contains a chelating agent such that the hyaluronic acid compacted using a salt can be swelled, the cosmetic of the present disclosure can provide a favorable moisture-retaining property with any chelating agent.

Figure 10:
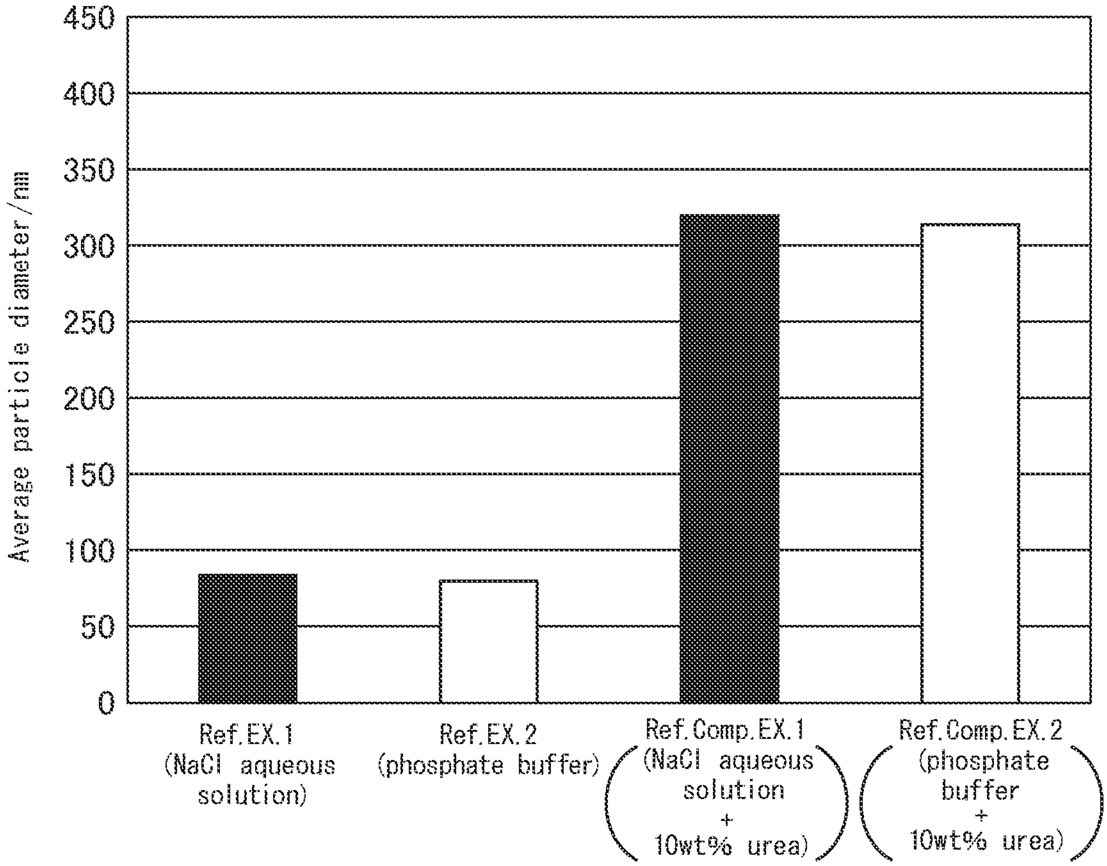
FIG. 10 is a graph related to the Z average particle diameter of hyaluronic acid particles to which urea was added.

The hyaluronic acid compacted with a salt can be swelled also by urea as shown in FIG. 10. However, the swelling by urea is swelling caused by breakage of the hydrogen bonds involved in the compaction, rather than swelling caused by a decreased electrostatic shielding effect.

«Cosmetic»

The cosmetic of the present disclosure comprises a first agent and a second agent.

<First Agent>

The first agent in the present disclosure contains: at least one salt selected from the group consisting of an inorganic salt and an organic acid salt; and hyaluronic acid.

(Salt)

The salt that may be included in the first agent of the present disclosure is not limited as long as the salt is capable of apparently neutralizing the negative charge of hyaluronic acid. Examples of such a salt include at least one salt selected from inorganic salts and organic acid salts. Taking use as a cosmetic into account, the salt, among inorganic salts and organic acid salts, is preferably a salt which hardly adversely affects the skin or body hair. Here, the term "inorganic salt" means a salt comprising only inorganic components, and this can also be said to be a salt formed by ions generated from an inorganic acid and an inorganic base. The term "organic acid salt" means a salt formed by an organic acid and a metal ion bound to each other. The salt in the first agent is generally present in the form of ions derived from the salt. Thus, in the present disclosure, the term "first agent containing a salt" means, for example, that the salt is contained in the form of such ions. Ionic surfactants are not included in the "salt" of the present disclosure.

Examples of the inorganic salts include sodium nitrate, sodium sulfate, sodium chloride, potassium nitrate, potassium sulfate, potassium chloride, calcium nitrate, calcium sulfate, calcium chloride, magnesium nitrate, magnesium sulfate, magnesium chloride, aluminum nitrate, aluminum sulfate, and aluminum chloride. These salts may be used individually, or as a combination of two or more thereof.

Examples of the organic acid salts include citrate, acetate, lactate, tartrate, succinate, malate, glycolate, salicylate, and pyrrolidone carboxylate. Specific examples thereof include salts in which an organic acid such as citric acid, acetic acid, lactic acid, tartaric acid, succinic acid, malic acid, glycolic acid, salicylic acid, or pyrrolidone carboxylic acid is bound to a metal ion such as sodium ion, potassium ion, calcium ion, magnesium ion, or aluminum ion. These salts may be used individually, or as a combination of two or more thereof.

From the viewpoint of the cation-capturing property of the chelating agent contained in the second agent described later, the cation constituting the salt is preferably a metal ion, more preferably a divalent or higher-valent metal ion.

The amount of the salt included in the first agent is not limited, and may be appropriately selected depending on the degree of compaction of the hyaluronic acid. The amount of the salt included may be, for example, 0.10% by mass or more, 0.20% by mass or more, 0.30% by mass or more, 0.40% by mass or more, or 0.50% by mass or more, and may be 5.0% by mass or less, 4.0% by mass or less, 3.0% by mass or less, 2.0% by mass or less, 1.9% by mass or less, 1.8% by mass or less, 1.7% by mass or less, 1.6% by mass or less, or 1.5% by mass or less, with respect to the total amount of the first agent.

The amount of the salt in the first agent can be defined also as the ionic strength of the salt. The ionic strength of the salt may be, for example, 0.01 or more, 0.03 or more, or 0.05 or more, and may be, for example, 5.0 or less, 4.0 or less, 3.0 or less, 2.0 or less, or 1.0 or less.

Here, for example, when the first agent is prepared by adding a salt to a buffer, the amount of the salt included or the ionic strength is calculated based on all salt components including the salt component (s) contained in the buffer itself and the salt component(s) separately added to the buffer.

(Hyaluronic Acid)

The hyaluronic acid that may be included in the first agent of the present disclosure is not limited. In general, hyaluronic acid means a linear polymer in which N-acetyl-D-glucosamine residues and D-glucuronic acid residues are alternately linked, and such hyaluronic acid can be obtained, for example, by isolation extraction from a cockscomb or another animal tissue, or by fermentation using a microorganism such as the genus *Streptococcus.*

The hyaluronic acid may be a derivative of hyaluronic acid. Examples of the hyaluronic acid derivative that may be used include metal salts of hyaluronic acid, such as the sodium salt of hyaluronic acid, the potassium salt of hyaluronic acid, the magnesium salt of hyaluronic acid, the calcium salt of hyaluronic acid, and the aluminum salt of hyaluronic acid; and hyaluronic acid derivatives obtained by etherification, esterification, amidation, acetylation, acetalization, or ketalization of a hydroxyl group, carboxyl group, or the like of hyaluronic acid. Here, "hyaluronic acid" in the present disclosure may encompass the concept of hyaluronic acid and derivatives thereof.

The weight average molecular weight of the hyaluronic acid is not limited, and may be, for example, 10,000,000 or less. From the viewpoint of the water-retaining performance of the hyaluronic acid, and the compaction of the hyaluronic acid, the weight average molecular weight of the hyaluronic acid may be, for example, 500 or more, 1000 or more, 5000 or more, 10,000 or more, 50,000 or more, 100,000 or more, 300,000 or more, 500,000 or more, 800,000 or more, or 1,000,000 or more, and may be, for example, 10,000,000 or less, 8,000,000 or less, 5,000,000 or less, 3,000,000 or less, 2,000,000 or less, or 1,500,000 or less. Here, the weight average molecular weight means the weight average molecular weight in terms of polystyrene in gel permeation chromatography measurement.

In some embodiments, the hyaluronic acid in the present disclosure may exhibit a form of a particle having an average particle diameter of 200 nm or less. A hyaluronic acid in such a form can easily penetrate into the skin or body hair.

For example, it can easily noninvasively penetrate into the skin through the stratum corneum or pores of the skin. It is generally considered that a hyaluronic acid having a relatively low molecular weight with a weight average molecular weight of less than 500 can be easily allowed to penetrate into the skin or body hair even without forming the hyaluronic acid into microparticles. However, since such a low-molecular-weight hyaluronic acid hardly stays in the skin or body hair, and its water-retaining performance is lower than that of a high-molecular-weight hyaluronic acid, it may be difficult to maintain the moisture-retaining effect in the skin or body hair over a long period of time. On the other hand, the hyaluronic acid particles in the present disclosure can be prepared using a hyaluronic acid having a weight average molecular weight of 500 or more, and such a hyaluronic acid can be included in the particles at a high level. As a result, the obtained hyaluronic acid particles tend to stay in the skin or body hair, and can maintain the moisture-retaining effect in the skin or body hair over a long period of time.

As the hyaluronic acid, hyaluronic acid and its derivatives may be used individually, or as a combination of two or more thereof. The hyaluronic acid and/or its derivative(s) used may have either the same molecular weight or different molecular weights.

A commercially available hyaluronic acid may be used. Examples of the commercially available hyaluronic acid include hyaluronic acid HA-LQ (manufactured by Kewpie Corporation), hyaluronic acid FCH (manufactured by Kikkoman Biochemical Company), and sodium bio-hyaluronate HA12N (manufactured by Shiseido Co., Ltd.).

The hyaluronic acid contained in the first agent in the present disclosure is thought to be shrunk due to the electrostatic shielding effect based on the salt, and the action of hydrogen bonding, to exhibit a form in which single hyaluronic acid molecules or a plurality of hyaluronic acid molecules entangled with each other are aggregated (such a form may be referred to as "hyaluronic acid aggregated/shrunken product"). Since a hyaluronic acid in such a form can be prepared without using the support materials as described in PTLs 1 and 2, the content ratio of hyaluronic acid in the hyaluronic acid aggregated/shrunken product can be theoretically 100% by mass. Thus, the hyaluronic acid aggregated/shrunken product of the present disclosure can be formed using hyaluronic acid molecules alone as a polymer component.

However, the hyaluronic acid aggregated/shrunken product of the present disclosure may also contain a polymer component other than hyaluronic acid as long as the moisture-retaining performance and the like are not deteriorated. The content ratio of the other polymer component may be, for example, 20% by mass or less, 10% by mass or less, 5% by mass or less, 3% by mass or less, or 1% by mass or less with respect to the total amount of the polymers contained in the hyaluronic acid aggregated/shrunken product. Thus, in the present disclosure, the "hyaluronic acid aggregated/shrunken product" may mean a product highly containing a hyaluronic acid component, and does not encompass particles in which the ratio of the hyaluronic acid component is 50% by mass or less such as those described in PTLs 1 and 2. Here, the content ratio of hyaluronic acid in the hyaluronic acid aggregated/shrunken product can be measured using, for example, the ELISA method.

In some embodiments, the amount of the salt added and/or the like may be adjusted to form the hyaluronic acid aggregated/shrunken product into a particle form having a filamentous-ball shape (this form may be further referred to as "hyaluronic acid particle") that can be measured by the dynamic light scattering method. The penetration of hyaluronic acid particles into the skin or body hair varies among individuals depending on, for example, the state of the stratum corneum, the state of the hair, and the number or size of the pores. However, in cases where the particles have an average particle diameter of 200 nm or less, the particles can be allowed to penetrate into the skin or body hair in most cases. From the viewpoint of the penetrability into the skin or body hair, ease of preparation of the particles, and the like, the average particle diameter of the hyaluronic acid particles may be, for example, 150 nm or less, 120 nm or less, or 100 nm or less, and may be 10 nm or more, 30 nm or more, or 50 nm or more. Here, the average particle diameter means the Z average particle diameter of the hyaluronic acid particles as optically measured by the dynamic light scattering method based on the assumption that the particle shape of the hyaluronic acid particles is spherical. Such an average particle diameter can be measured using, for example, a Zetasizer (manufactured by Malvern Panalytical Co., Ltd.), or a dynamic light scattering photometer DLS-8000 (manufactured by Otsuka Electronics Co., Ltd.). These measuring devices can be appropriately selected based on the overlap concentration of each hyaluronic acid. For example, a dynamic light scattering photometer DLS-8000 can be used when the hyaluronic acid concentration is less than the overlap concentration, and a Zetasizer can be used when the hyaluronic acid concentration is the overlap concentration or more. The overlap concentration can be calculated, for example, by the confocal fluorescence recovery after photobleaching method (Confocal-FRAP).

It is thought that, although hyaluronic acid particles having an average particle diameter of 200 nm or less can penetrate into the skin or body hair, they can hardly stay in the skin or body hair because of their small particle diameter. The cosmetic of the present disclosure can swell such particles by the application of the second agent, which contains a chelating agent, to the hyaluronic acid particles. In other words, after allowing hyaluronic acid to penetrate into the skin or body hair, the hyaluronic acid can be swelled in the skin or body hair by the application of the second agent. Therefore, the hyaluronic acid can be retained in the skin or body hair. As a result, the moisture-retaining effect in the skin or body hair can be maintained over a longer period of time.

From the viewpoint of the moisture-retaining property, the cost, and the like, the content of the hyaluronic acid in the first agent may be, for example, 0.005% by mass or more, 0.01% by mass or more, 0.05% by mass or more, 0.10% by mass or more, 0.15% by mass or more, 0.20% by mass or more, or 0.25% by mass or more, and may be, for example, 1.0% by mass or less, 0.80% by mass or less, 0.60% by mass or less, 0.50% by mass or less, or 0.45% by mass or less, with respect to the total amount of the first agent. As described above, the hyaluronic acid contained in the first agent of the present disclosure has a high content ratio of hyaluronic acid in the hyaluronic acid aggregated/shrunken product. Moreover, due to the action of the chelating agent in the second agent, the hyaluronic acid has an excellent hydration capacity based on the carboxyl groups of the hyaluronic acid. Therefore, a sufficient moisture-retaining effect can be exhibited even in cases where the hyaluronic acid content in the first agent is relatively low.

(Aqueous Medium)

The first agent of the present disclosure may typically contain an aqueous medium. The aqueous medium is not limited, and aqueous media used in cosmetics, quasi-drugs, and the like may be used. Examples of the aqueous media that may be used include ion-exchanged water, distilled water, ultrapure water, tap water, and buffers. These aqueous media may be used individually, or as a combination of two or more thereof.

Examples of the buffers include citrate buffer, lactate buffer, phosphate buffer, acetate buffer, tartrate buffer, borate buffer, and Tris buffer. From the viewpoint of securing a high buffer capacity, citrate buffer, lactate buffer, and phosphate buffer are preferred. Citrate buffer is more preferred.

The pH of the buffer may be 7.0 or less, 6.8 or less, or 6.5 or less. There is no lower limit value of the pH of the buffer. From the viewpoint of, for example, reducing irritation to the skin or body hair, the pH is preferably 4.5 or more, 5.5 or more, or 6.0 or more.

<Second Agent>

The second agent of the present disclosure contains a chelating agent, and is capable of swelling the hyaluronic acid described above. The term "capable of swelling the hyaluronic acid" means, in other words, that the chelating agent is contained, in the second agent, in an amount within a range in which the hyaluronic acid can be swelled as shown in FIG. 1 or FIG. 2. It can be said that, in cases where the chelating agent is contained in the second agent at a ratio which allows the swelling of the hyaluronic acid, cations that are neutralizing carboxyl groups of the hyaluronic acid can be sufficiently captured by the chelating agent. By the release of the cations, the carboxyl groups of the hyaluronic acid become capable of sufficiently exerting the ability to hold water (hydration capacity), and moreover, the swelled hyaluronic acid has an increased water-retaining property compared to compacted hyaluronic acid. Therefore, such hyaluronic acid can provide a favorable moisture-retaining property for the skin.

The swelling of hyaluronic acid means that the volume of the hyaluronic acid in the first agent increases by the application of the second agent to the first agent. This increase in the volume of the hyaluronic acid can be evaluated by the ratio based on the particle diameter (which may be referred to as "relative particle diameter") or the ratio based on the partial specific volume (which may be referred to as "partial specific volume ratio").

The relative particle diameter may be more than 1.00, 1.10 or more, 1.20 or more, or 1.30 or more. The upper limit value of the relative particle diameter is not restricted. The relative particle diameter may be, for example, 3.00 or less, 2.50 or less, 2.00 or less, or 1.80 or less. Here, the "relative particle diameter" means the value calculated by the following Equation 1:

Relative particle diameter=average particle diameter of hyaluronic acid particles in the first agent containing a predetermined amount of a chelating agent/average particle diameter of hyaluronic acid particles in the first agent containing no chelating agent  Equation 1

The partial specific volume ratio may be more than 1.00, 1.01 or more, or 1.02 or more. The upper limit value of the partial specific volume ratio is not restricted. The partial specific volume ratio may be, for example, 1.20 or less, 1.15 or less, or 1.10 or less. Here, the "partial specific volume" is the amount of change (cm$^3$/g) in the total volume caused by dissolving 1 g of hyaluronic acid in an infinite amount of solvent while the temperature, the pressure, and the concentrations of all other components are set constant. The "partial specific volume" means the value calculated by the following Equation 2. The "partial specific volume ratio" means the value calculated by the following Equation 3.

$$V^0_{sp,hya} = \frac{1}{\rho}\left[1 - \frac{1 - w_{hya}}{\rho}\frac{\partial\rho}{\partial w_{hya}}\right] \qquad \text{Equation 2}$$

(In Equation 2, $V^0_{sp,hya}$ is the partial specific volume of hyaluronic acid;

$\rho$ is the density of the aqueous hyaluronic acid solution; and $w_{hya}$ is the weight ratio of hyaluronic acid.)

Partial specific volume ratio=partial specific volume of hyaluronic acid in a state where a predetermined amount of a chelating agent is included in the first agent/partial specific volume of hyaluronic acid in the first agent containing no chelating agent  Equation 3

(Chelating Agent)

The chelating agent that may be included in the second agent of the present disclosure is not limited as long as the chelating agent is capable of capturing cations electrostatically shielding the negative charge of carboxyl groups of the hyaluronic acid, to cause swelling of the hyaluronic acid. Examples of such a chelating agent include ethylenediaminetetraacetic acid, disodium ethylenediaminetetraacetate, trisodium ethylenediaminetetraacetate, nitrilotriacetic acid, sodium nitrilotriacetate, ammonium nitrilotriacetate, hydroxyethylethylenediaminetriacetic acid, sodium hydroxyethylethylenediaminetriacetate, pentetic acid, pentasodium pentetate, triethylenetetramine hexaacetic acid, sodium triethylenetetramine hexaacetate, imidisuccinic acid, tetrasodium imidisuccinate, ethylenediaminedisuccinic acid, trisodium ethylenediamine disuccinate, hydroxyethyliminodiacetic acid, disodium hydroxyethyliminodiacetate, iminodisuccinic acid, tetrasodium iminodisuccinate, triethylenetetramine hexaacetic acid, sodium triethylenetetramine hexaacetate, methylglycine diacetic acid, trisodium methylglycine diacetate, hydroxyiminodisuccinic acid, tetrasodium hydroxyiminodisuccinate, L-aspartic acid diacetic acid, tetrasodium L-aspartate diacetate, glutamic acid diacetic acid, tetrasodium glutamate diacetate, propanediaminetetraacetic acid, diammonium ethylenediaminetetraacetate, 1,3-diamino-2-hydroxypropane-tetraacetic acid, 1,3-diamino-2-hydroxypropane-tetraacetic acid, N,N-bis(2-hydroxyethyl) glycine, glycol ether diamine tetraacetic acid, dicarboxymethyl glutamic acid, tetrasodium dicarboxymethyl glutamate, diethylenetriaminepentaacetic acid, hexametaphosphoric acid, sodium hexametaphosphate, nitrilotris (methylenephosphonic acid), potassium nitrilotris (methylenephosphonate), 2-phosphonobutane-1,2,4-tricarboxylic acid, ethylenediaminetetramethylene phosphonic acid, pentasodium ethylenediaminetetramethylene phosphonate, phytic acid, and citric acid. The chelating agents may be used individually, or as a combination of two or more thereof. In particular, from the viewpoint of the cation-capturing property, and the moisture-retaining effect of the hyaluronic acid by the capture of cations, the chelating agent is preferably disodium ethylenediaminetetraacetate (EDTA), hydroxyethyliminodiacetic acid (HIDA), diethylenetriaminepentaacetic acid (DTPA), nitrilotriacetic acid, phytic acid, or sodium hexametaphosphate (HMP).

The amount of the chelating agent included in the second agent may be appropriately set depending on the type and the amount of the hyaluronic acid or the salt in the first agent, and the type of the chelating agent, such that the relative particle diameter or the partial specific volume ratio of the hyaluronic acid increases.

For example, in cases where disodium ethylenediaminetetraacetate is used as the chelating agent, the amount of substance of the chelating agent with respect to 100 mol of the salt (=(molar concentration of the chelating agent/molar concentration of the salt)×100) may be 0.001 or more, 0.01 or more, 0.05 or more, 0.07 or more, 0.10 or more, 0.15 or more, 0.20 or more, 0.25 or more, or 0.30 or more, and may be 10 or less, 7.0 or less, 5.0 or less, 3.0 or less, 2.0 or less, 1.7 or less, or 1.5 or less.

For example, in cases where sodium hexametaphosphate is used as the chelating agent, the amount of substance of the chelating agent with respect to 100 mol of the salt (=(molar concentration of the chelating agent/molar concentration of the salt)×100) may be 0.1 or more, 0.5 or more, 1.0 or more, 1.2 or more, 1.5 or more, 1.7 or more, or 2.0 or more, and may be 20 or less, 15 or less, 10 or less, 7.0 or less, 5.0 or less, 4.5 or less, or 4.0 or less.

(Aqueous Medium)

The second agent of the present disclosure may typically contain an aqueous medium. The aqueous medium is not limited, and aqueous media used in cosmetics, quasi-drugs, and the like may be used. Examples of the aqueous media that may be used include ion-exchanged water, distilled water, ultrapure water, and tap water. These aqueous media may be used individually, or as a combination of two or more thereof.

<Optional Components>

In the first agent and the second agent of the cosmetic of the present disclosure, various components may be included, when appropriate, within a range that does not affect the effect of the present invention. Examples of such components include skin or hair nutrients; vitamins; water-soluble agents applicable to pharmaceuticals, quasi-drugs, cosmetics, and the like; ultraviolet absorbers; antioxidants; preservatives; antioxidant aids; thickeners; pigments; dyes; colorants; and fragrances. These optional components may be used individually, or as a combination of two or more thereof.

«Preparation Method for Cosmetic»

The first agent and the second agent of the cosmetic of the present disclosure may be prepared, for example, using the following method. As materials such as the hyaluronic acid, salt, chelating agent, water, buffer, and optional components that may be used in the preparation method for the first agent and the second agent, the above-described materials may be used.

<Preparation Method for First Agent>

The first agent can be prepared by adding a salt to water or a buffer to prepare a solution, adding hyaluronic acid to the resulting solution, and then dissolving the hyaluronic acid with stirring and mixing.

Alternatively, the first agent can be prepared by adding hyaluronic acid to water or a buffer, dissolving the hyaluronic acid with stirring and mixing, and then adding a salt to the resulting solution.

In cases where the buffer itself exhibits the above-described salt concentration or ionic strength by the action of the salt contained in the buffer, the addition of the salt can be omitted.

In cases where the optional components described above are to be included, such optional components may be added before the compaction of the hyaluronic acid using the salt, but the optional components are preferably added after the preparation of the compacted hyaluronic acid so as not to affect the compacted hyaluronic acid.

<Preparation Method for Second Agent>

The second agent can be prepared by adding a chelating agent to water, and stirring and mixing the resulting mixture.

«Application Site of Cosmetic»

The cosmetic of the present disclosure is applicable to any part of the body. For example, the cosmetic may be applied to any part on the skin surface (body surface) or on the body hair (hair). More specifically, the cosmetic of the present disclosure may be applied, when appropriate, to the skin surface of the face (lips, eyes, eyelids, cheeks, forehead, glabella, nose, or the like), head (scalp), ears, hands, arms, neck, legs, feet, chest, abdomen, back, or the like, or to a body hair such as hair, eyebrows, lashes, or mustache. Here, the skin also includes nails and the like formed by hardening of the corneum of the skin epidermis. The body hair means hairs grown on the body. In the present disclosure, "body hair" can also be referred to as "hair". Thus, the cosmetic of the present disclosure can be suitably used as a cosmetic for the skin or a cosmetic for hair.

«Cosmetic Method Using Cosmetic»

The cosmetic method using the cosmetic of the present disclosure comprises: applying the first agent described above to a body surface or body hair; and then applying the second agent described above to the application area of the first agent. In the present disclosure, "cosmetic method" means a method of beautifying a body surface or body hair by achieving a beautiful and orderly condition of the body surface or body hair by application of the cosmetic of the present disclosure to the body surface or body hair. The method is thus different from a method of operation, treatment, or diagnosis of a human.

In general, one unknowingly suffers from deprivation of moisture from skin or body hair when the skin or body hair is exposed to dryness, which deprivation leads to a state where the water content on the surface of the skin or body hair cannot be maintained. For example, when the moisture on the skin surface is insufficient, a moisturizing component to be produced by the skin itself (Natural Moisturizing Factor (NMF)) cannot be successfully produced. As a result, the barrier function and the moisturizing function on the skin surface deteriorate, and the skin tends to be damaged. This has been thought to result in loss of moisture, formation of wrinkles, skin roughness, and the like. Further, it has been thought that dryness of hairs due to loss of moisture causes formation of split ends, hair breakage, easy spreading of the hairs due to static electricity, and the like.

By the cosmetic of the present disclosure, compacted hyaluronic acid can be allowed to stay in grooves, pores, or the like of the skin, or to adsorb on the surface of the body hair. Further, in some cases, after the hyaluronic acid penetrates into the skin or body hair, cations such as sodium ions that have been neutralizing the negative charge of carboxyl groups in the hyaluronic acid can be captured. By this, the hyaluronic acid can be swelled to allow sufficient exertion of the moisture-retaining property of the hyaluronic acid itself, thereby enabling favorable moisturization of the skin or body hair. As a result, for example, the function that allows the skin itself to generate the moisturizing component can be improved, and moreover, poor turnover in the stratum corneum can be improved, or moisture of hair can be improved. Therefore, troubles such as skin roughness, or formation of split ends or hair breakage can be reduced to enhance the cosmetic effect.

The means of application of the first agent and the second agent to the body surface or body hair is not limited. For example, the application may be performed by applying the first agent and the second agent onto the body surface or body hair. Regarding the means of applying the first agent and the second agent onto the body surface or body hair, the application may be carried out by spraying the first agent and the second agent onto the skin or body hair using a spray container for each agent. Alternatively, the application may be carried out by placing each of the first agent and the second agent in a container having no spray function, collecting an appropriate amount of the first agent or the second agent on a finger or palm or the like, followed by spreading each of the first agent and the second agent on the body surface or body hair.

EXAMPLES

Hereinafter, the present invention will be described in more detail with reference to Test Examples and Examples, but the present invention is not limited thereto.

Test Examples 1 to 4

<Evaluation of Skin Cosmetics>

Each test sample obtained by the following production methods was subjected to the evaluations described below. The results are summarized in Tables 1 to 5 and FIGS. 1 to 4.

(Evaluation of Relative Particle Diameter: Swelling Property of Hyaluronic Acid)

The average particle diameter of hyaluronic acid particles in the test sample was evaluated based on the Z average particle diameter according to the dynamic light scattering method using a Zetasizer (manufactured by Malvern Panalytical Co., Ltd.). The relative particle diameter was calculated from the obtained average particle diameter and the following Equation 4.

Relative particle diameter=average particle diameter of hyaluronic acid particles in a test sample containing a predetermined amount of a chelating agent/average particle diameter of hyaluronic acid particles in a test sample containing no chelating agent  Equation 4

(Evaluation of Amount of Stratum Corneum Water Content)

After washing the inner part of an upper arm of a subject with soap (SAVON D'OR (registered trademark)), the subject was made to stay in a constant temperature and humidity room at a temperature of 25±1° C. and a relative humidity of 50±5% for 15 minutes, to perform environment control for the subject. Subsequently, the water content of the skin surface of the washed inner part of the upper arm before application of the test sample, and the water contents of the skin surface at Minute 30 and Minute 90 after applying 18 μl of the test sample thereto at a ratio of 2 $\mu l/cm^2$, were measured using a Corneometer (registered trademark) CM825 (manufactured by Courage and Khazaka Co., Ltd.). In cases of use of a second agent containing a chelating agent, a first agent in the amount described above was applied to the skin, and then the second agent was applied to the application area in the amount described above. In Table 4, each value of the water content is the average from six replicates, and "difference" represents the value calculated by subtracting the actual measured value before the application from each actual measured value.

(Evaluation of Texture Count)

After washing the inner part of an upper arm of a subject with soap (SAVON D'OR (registered trademark)), the subject was made to stay in a constant temperature and humidity room at a temperature of 25±1° C. and a relative humidity of 50±5% for 15 minutes, to perform environment control for the subject. Subsequently, the texture count of the skin surface of the washed inner part of the upper arm before application of the test sample, and the texture counts of the skin surface at Minute 30 and Minute 90 after applying 18 μl of the test sample thereto at a ratio of 2 $\mu l/cm^2$, were measured using a Handy Skin Sensor II (manufactured by Shiseido Co., Ltd.). In cases of use of a second agent containing a chelating agent, a first agent in the amount described above was applied to the skin, and then the second agent was applied to the application area in the amount described above. Each value of the texture count in Table 5 represents the average from six replicates.

Test Example 1: Effect of Chelating Agent

In Test Example 1, the effect of a chelating agent on hyaluronic acid compacted by inclusion of a salt was studied. The results are shown in Tables 1 and 2, and FIGS. 1 and 2. Here, the amount of substance of the chelating agent (HMP) is the amount of substance in terms of metaphosphoric acid ($P_2O_5$).

(Method of Preparing Test Samples)

Hyaluronic acid (manufactured by Shiseido Co., Ltd., Biohyaluro 12: weight average molecular weight 1.2 million) was added to ion-exchanged water to a content of 0.5% by mass, and the resulting mixture was stirred and mixed by a vortex mixer, to prepare Composition A. After dissolving the hyaluronic acid, magnesium chloride hexahydrate ($MgCl_2.6H_2O$) was added at a concentration of 0.46% by mass, 0.91% by mass, or 1.42% by mass, or sodium chloride was added at a concentration of 0.82% by mass or 1.23% by mass, to aliquots of Composition A, and each resulting mixture was stirred and mixed by a vortex mixer, to prepare a test sample containing no chelating agent.

Subsequently, to each test sample containing no chelating agent, sodium hexametaphosphate (HMP) as a chelating agent was added at the concentration shown in Table 1 and Table 2, and the resulting mixture was stirred and mixed by a vortex mixer, to prepare a test sample containing no chelating agent.

TABLE 1

| $MgCl_2$ concentration (% by mass) | Molar concentration (mol/L) | Ionic strength | Concentration of chelating agent (HMP) (% by mass) | | | | | | | | |
|---|---|---|---|---|---|---|---|---|---|---|---|
| | | | 0 | 0.01 | 0.02 | 0.03 | 0.04 | 0.05 | 0.06 | 0.07 | 0.10 |
| | | | Concentration of chelating agent (HMP) (mmol/L) | | | | | | | | |
| | | | 0 | 0.49 | 0.99 | 1.48 | 1.97 | 2.47 | 2.96 | 3.45 | 4.93 |
| | | | Relative particle diameter | | | | | | | | |
| 0.46 | 0.02 | 0.07 | 1.00 | — | 1.13 | — | 0.95 | — | 0.92 | — | — |
| 0.91 | 0.04 | 0.13 | 1.00 | 1.02 | 1.15 | 1.16 | 1.13 | 1.17 | 1.08 | 0.90 | 0.97 |
| 1.42 | 0.07 | 0.21 | 1.00 | 1.22 | 1.20 | 1.36 | 1.17 | 1.01 | — | 0.99 | — |

TABLE 2

| NaCl concentration (% by mass) | Molar concentration (mol/L) | Ionic strength | Concentration of chelating agent (HMP) (% by mass) 0 / (mmol/L) 0 | 0.05 / 2.47 | 0.10 / 4.93 | 0.15 / 7.40 | 0.20 / 9.86 |
|---|---|---|---|---|---|---|---|
| | | | Relative particle diameter | | | | |
| 0.82 | 0.14 | 0.14 | 1.00 | 1.05 | 1.33 | 1.10 | 0.96 |
| 1.23 | 0.21 | 0.21 | 1.00 | 1.40 | 1.78 | 1.49 | 0.98 |

(Results)

As is apparent from the results in Tables 1 and 2 and FIGS. 1 and 2, it could be confirmed that inclusion of a chelating agent at a predetermined ratio to hyaluronic acid compacted by addition of a salt results in an increased relative particle diameter of the hyaluronic acid, that is, swelling of the hyaluronic acid. The swelling of the hyaluronic acid is thought to be due to the fact that the chelating agent captures cations electrostatically shielding the negative charge of carboxyl groups of the hyaluronic acid.

In this test, the evaluation was carried out by adding a chelating agent to a sample bottle containing a salt and hyaluronic acid. It can be assumed, however, that swelling of hyaluronic acid may similarly occur also in cases where an agent containing a salt and hyaluronic acid is applied to the skin, and then an agent containing a chelating agent is applied to the application area.

Test Example 2: Type of Chelating Agent

In Test Example 2, the swelling property of hyaluronic acid compacted by addition of a salt was studied for cases where a chelating agent other than sodium hexametaphosphate (HMP) was used. The results are shown in Table 3. Here, "control" in Table 3 represents a test sample containing a salt and hyaluronic acid, but not containing a chelating agent, which test sample was used as a standard for comparison of the relative particle diameter. In Table 3, "EDTA" means disodium ethylenediaminetetraacetic acid; "HIDA" means hydroxyethyliminodiacetic acid; and "DTPA" means diethylenetriaminepentaacetic acid.

(Method of Preparing Test Samples)

Using the chelating agents described in Table 3, test samples were prepared by the same method as in Test Example 1. As the salt, magnesium chloride hexahydrate ($MgCl_2.6H_2O$) was used at a salt concentration of 1.42% by mass. Each chelating agent was used at a concentration of 0.03% by mass.

TABLE 3

| Chelating agent | Relative particle diameter |
|---|---|
| Control | 1.00 |
| HMP | 1.36 |
| EDTA | 1.11 |
| HIDA | 1.10 |

TABLE 3-continued

| Chelating agent | Relative particle diameter |
|---|---|
| DTPA | 1.59 |
| Nitrilotriacetic acid | 1.10 |
| Phytic acid | 1.35 |

(Results)

As is apparent from the results in Table 3, it could be confirmed that swelling of the hyaluronic acid occurs also by the use of a chelating agent other than sodium hexametaphosphate (HMP).

Test Example 3: Evaluation of Moisture-Retaining Property (Stratum Corneum Water Content)

In Test Example 3, the moisture-retaining property was evaluated by studying changes in the stratum corneum water content with time in each test sample. The results are shown in Table 4 and FIG. 3.

Example 1

Hyaluronic acid (manufactured by Shiseido Co., Ltd., Biohyaluro 12: weight average molecular weight 1.2 million) was added to ion-exchanged water to a content of 0.5% by mass, and the resulting mixture was stirred and mixed by a vortex mixer, to prepare a composition. To this composition, magnesium chloride hexahydrate ($MgCl_2.6H_2O$) was added at a concentration of 1.42% by mass, and the mixture was stirred and mixed by a vortex mixer, to prepare a test sample of a first agent.

Subsequently, sodium hexametaphosphate (HMP) as a chelating agent was added at a concentration of 0.03% by mass to ion-exchanged water, and the mixture was stirred and mixed by a vortex mixer, to prepare a test sample of a second agent.

Comparative Example 1

The first agent of Example 1 was used as the test sample of Comparative Example 1.

Comparative Example 2

The second agent of Example 1 was used as the test sample of Comparative Example 2.

TABLE 4

| | Example 1 (hyaluronic acid + salt + chelating agent) | | Comparative Example 1 (hyaluronic acid + salt) | | Comparative Example 2 (chelating agent) | |
|---|---|---|---|---|---|---|
| | Stratum corneum water content | | | | | |
| | Actual measured value | Difference | Actual measured value | Difference | Actual measured value | Difference |
| Before application | 22.67 | 0 | 22.65 | 0 | 23.25 | 0 |
| Minute 30 | 28.17 | 5.50 | 25.23 | 2.58 | 25.67 | 2.42 |
| Minute 90 | 28.50 | 5.83 | 24.84 | 2.19 | 25.42 | 2.17 |

(Results)

Figure 3:
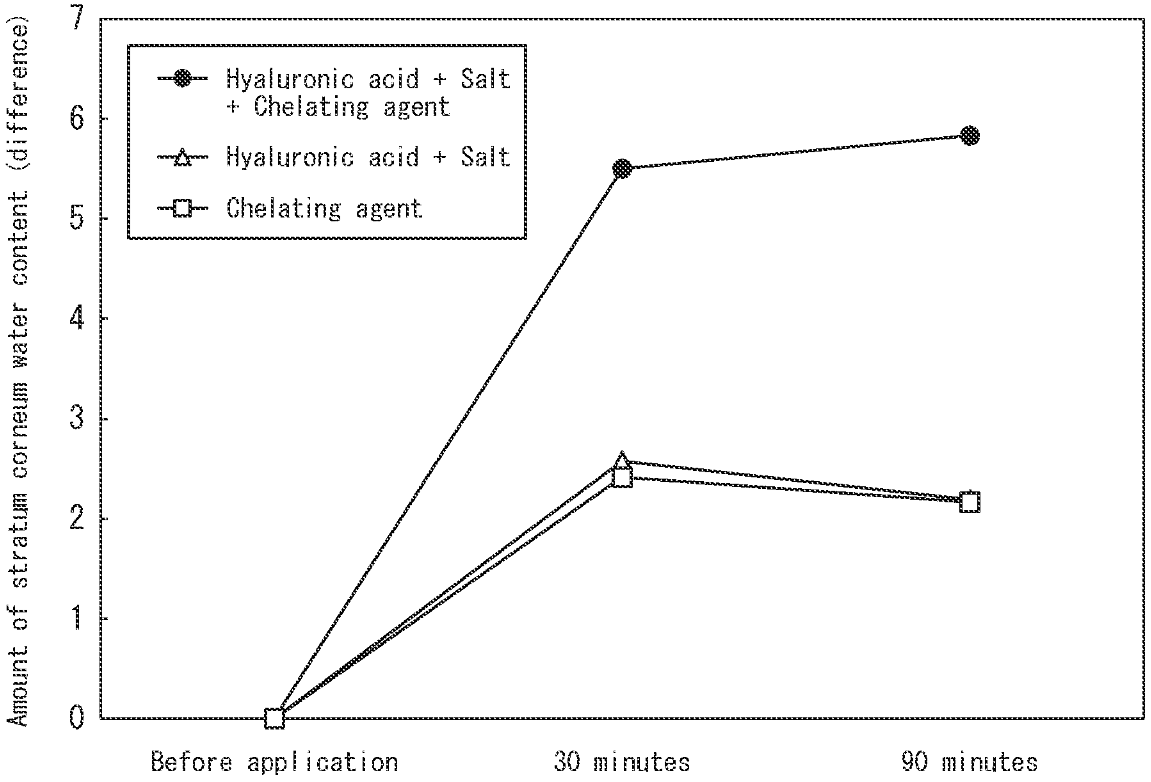
FIG. 3 is a graph related to changes in the stratum corneum water content based on comparison between the stratum corneum water contents before and after application of each test sample to the skin.

As is apparent from the results in Table 4 and FIG. 3, it could be confirmed that, when hyaluronic acid compacted by addition of a salt is applied to the skin, and a chelating agent is applied thereafter, the stratum corneum water content remarkably increases. This is thought to be due to the following reason. The chelating agent captures magnesium ions that have been neutralizing the negative charge of carboxyl groups of the hyaluronic acid. As a result, the moisture-retaining performance of the hyaluronic acid itself is sufficiently produced, and at the same time, swelling of the hyaluronic acid occurs to increase the water-retaining property. The result on the capture of cations by the chelating agent is consistent with the results in Tables 1 and 2 and FIGS. 1 and 2.

Test Example 4: Evaluation of Moisture-Retaining Property (Texture Count of Skin)

In Test Example 4, the moisture-retaining property was evaluated by studying changes in the texture count of the skin with time in each test sample. The results are shown in Table 5 and FIG. 4.

Example 2

The first agent and the second agent of Example 1 were used as the test sample of Example 2.

Comparative Example 3

The first agent of Example 1 was used as the test sample of Comparative Example 3.

Comparative Example 4

The second agent of Example 1 was used as the test sample of Comparative Example 4.

TABLE 5

| | Example 2 (hyaluronic acid + salt + chelating agent) | Comparative Example 3 (hyaluronic acid + salt) | Comparative Example 4 (chelating agent) |
|---|---|---|---|
| | Texture count | | |
| Before application | 172.1 | 164.8 | 164.4 |
| Minute 30 | 223.5 | 166.5 | 164.8 |
| Minute 90 | 239.1 | 161.0 | 177.3 |

(Results)

Figure 4:
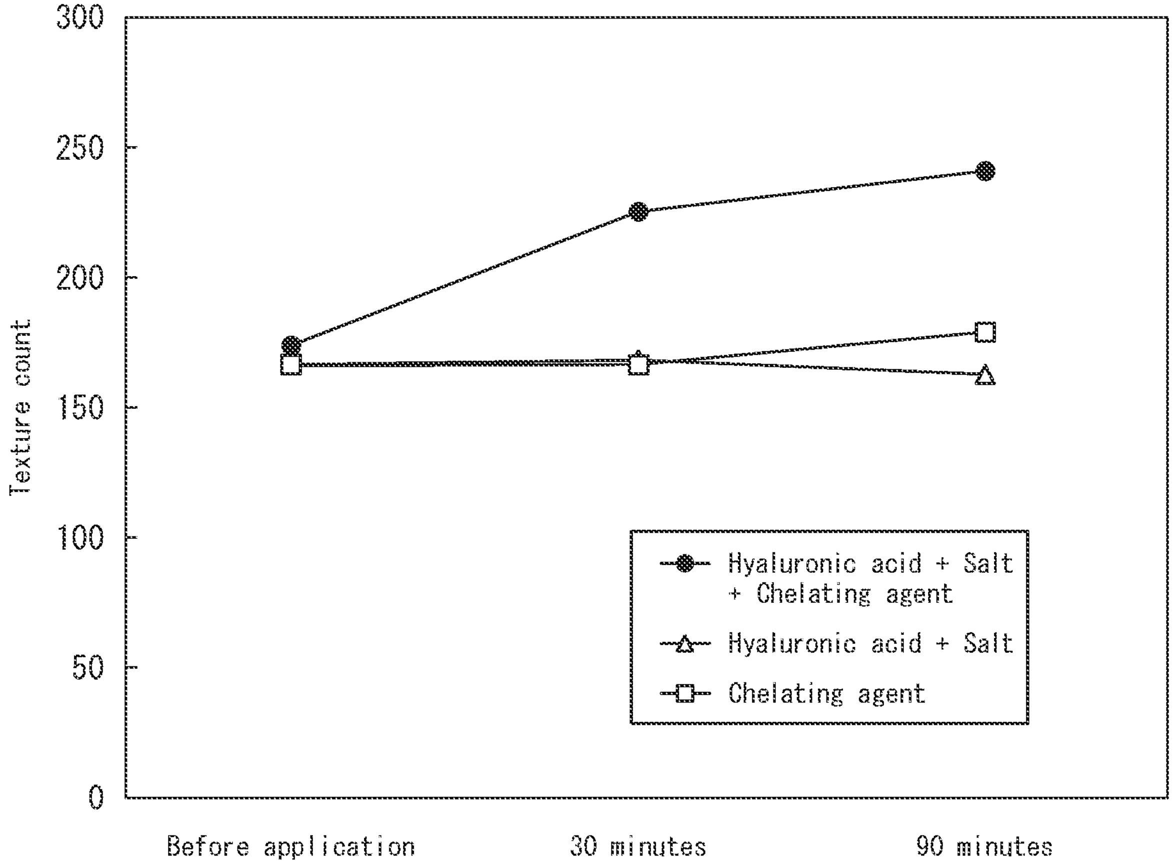
FIG. 4 is a graph related to changes in the texture count based on comparison between the texture counts before and after application of each test sample to the skin.

As is apparent from the results in Table 5 and FIG. 4, it could be confirmed that, when hyaluronic acid compacted by addition of a salt is applied to the skin, and a chelating agent is applied thereafter, the texture count of the skin increases. This is thought to be due to the fact that, as shown by the results in Table 4 and FIG. 3, the application of the first agent and the second agent of Example 1 increases the stratum corneum water content, resulting in a plump and orderly skin texture.

Reference Test Examples 1 to 6

For reference, the fact that use of a salt enables compaction of hyaluronic acid into a particle-like shape, and actions of such hyaluronic acid particles, are described below.

<Evaluation of Compositions>

The evaluations described below were performed on compositions obtained by the following manufacturing methods. The results are summarized in Tables 6 to 11 and FIGS. 5 to 10. In the tables and figures, "HA" means hyaluronic acid.

(Evaluation of Average Particle Diameter)

The average particle diameter of the hyaluronic acid particles in each composition was evaluated based on the Z average particle diameter according to the dynamic light scattering method using a Zetasizer (manufactured by Malvern Panalytical Co., Ltd.), or a dynamic light scattering photometer DLS-8000 (manufactured by Otsuka Electronics Co., Ltd.).

(Evaluation of Water Content Ratio)

After washing the inner part of an upper arm of a subject with soap, the subject was made to stay in a constant temperature and humidity room at a temperature of 21±1° C. and a relative humidity of 45±5% for 20 minutes, to perform environment control for the subject. Subsequently, the water content of the skin surface of the washed inner part of the upper arm before application of the composition, and the water contents of the skin surface at Minute 20, Minute 30, Minute 60, and Minute 120 after applying one drop (2×2 $cm^2$) of the composition thereto, were measured using a Corneometer (registered trademark) CM825 (manufactured by Courage and Khazaka Co., Ltd.). From each obtained water content, the water content ratio was calculated by the following Equation 5:

Water content ratio=water content after application of the composition/water content before application of the composition     Equation 5

Reference Test Example 1: Effect of Ionic Strength

In Reference Test Example 1, the effect of the ionic strength on the particle diameter of hyaluronic acid particles was studied. The results are shown in Table 6 and FIG. 5.

(Method for Preparing Compositions)

Hyaluronic acid (manufactured by Shiseido Co., Ltd., Biohyaluro 12: weight average molecular weight 1.2 million) was added to ion-exchanged water to a content of 0.1% by mass, and the resulting mixture was stirred and mixed by a vortex mixer, to prepare Composition B. After dissolving the hyaluronic acid, sodium chloride was added at a concentration of 0.001 M (mol/l), 0.003 M, 0.01 M, 0.02 M, 0.03 M, or 0.10 M to aliquots of Compositions B so that the ionic strength of the salt was 0.001, 0.003, 0.01, 0.02, 0.03, or 0.10, and each resulting mixture was stirred and mixed by a vortex mixer, to prepare a hyaluronic acid particle-containing composition. Here, since sodium chloride is composed of a monovalent cation and a monovalent negative charge, the concentration of sodium chloride and the value of the ionic strength are the same.

TABLE 6

| | Ionic strength | | | | | | |
|---|---|---|---|---|---|---|---|
| HA concentration 0.1% by mass | 0 | 0.001 | 0.003 | 0.01 | 0.02 | 0.03 | 0.1 |
| Average particle diameter (nm) | 2,254 | 493 | 308 | 204 | 208 | 56 | 83 |

(Results)

Figure 5:
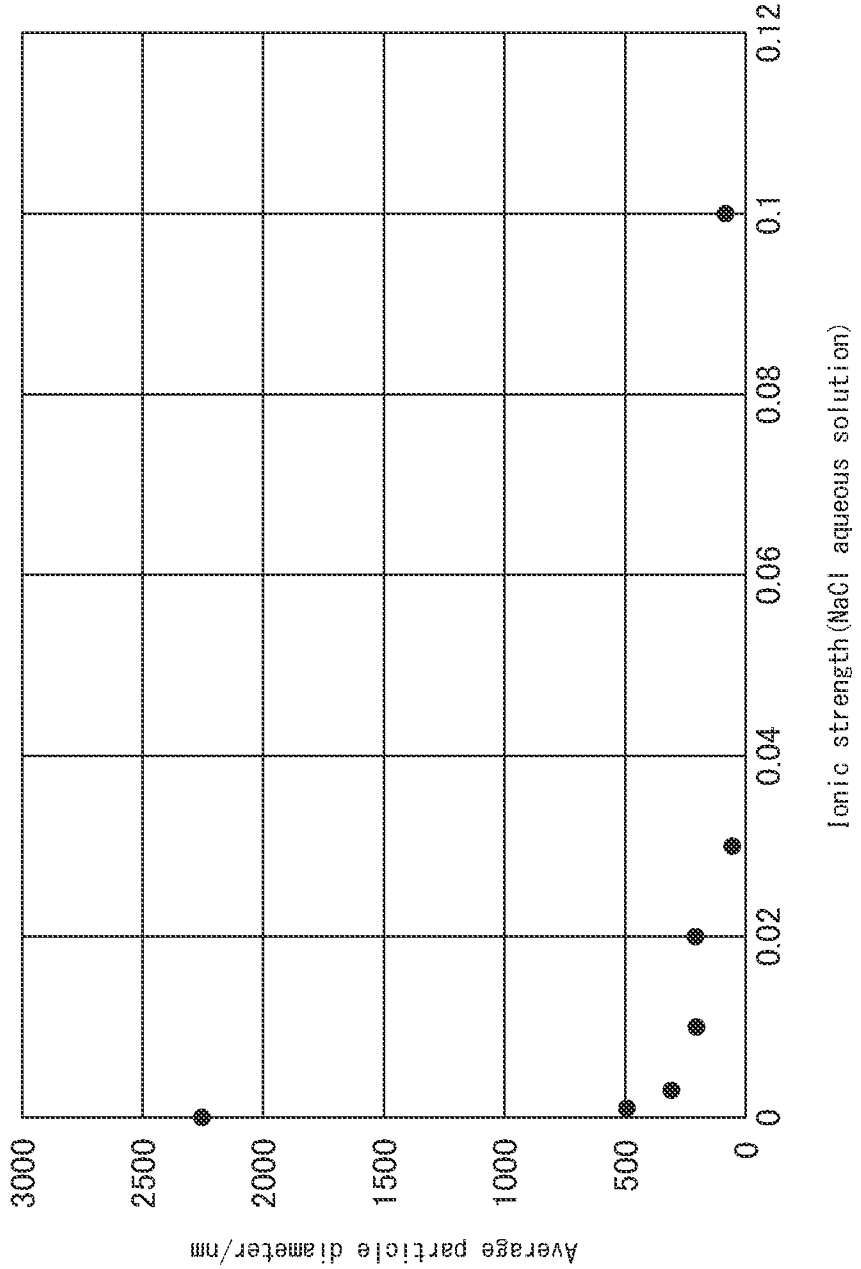
FIG. 5 is a graph related to the Z average particle diameter and the ionic strength of hyaluronic acid particles prepared using sodium chloride.

As is apparent from the results in Table 6 and FIG. 5, it could be confirmed that nanoscale hyaluronic acid particles can be obtained by the addition of the salt. In addition, it could be confirmed that, as the amount of the salt added increases, that is, as the ionic strength increases, the particle diameter of the hyaluronic acid particles tends to decrease, and that, in particular, at an ionic strength of 0.03 or more, hyaluronic acid particles with a diameter of 100 nm or less can be obtained.

Reference Test Example 2: Effects of Concentration and Ionic Strength of Hyaluronic Acid In Reference Test Example 2, the effects of the concentration and the ionic strength of hyaluronic acid at the time of preparation of the composition, on the particle diameter of the hyaluronic acid particles were studied. The results are shown in Table 7 and FIG. 6.

(Method for Preparing Compositions)

Hyaluronic acid particle-containing compositions were each prepared in the same manner as in Reference Test Example 1, except that the concentration of hyaluronic acid at the time of preparation of the composition was 0.01% by mass, 0.1% by mass, 0.2% by mass, 0.3% by mass, 0.4% by mass, or 0.5% by mass, and that sodium chloride was added such that the ionic strength was at the ratio described in Table 7.

TABLE 7

| | HA concentration | Ionic strength | | | | |
|---|---|---|---|---|---|---|
| | (% by mass) | 0.03 | 0.04 | 0.05 | 0.10 | 1.0 |
| Average particle diameter (nm) | 0.01 | — | — | 121 | 105 | 109 |
| | 0.1 | 59 | — | 56 | 64 | — |
| | 0.2 | 156 | 122 | — | — | — |
| | 0.3 | 211 | — | 66 | 57 | — |
| | 0.4 | — | — | 161 | 123 | — |
| | 0.5 | 367 | — | 187 | 190 | — |

(Results)

Figure 6:
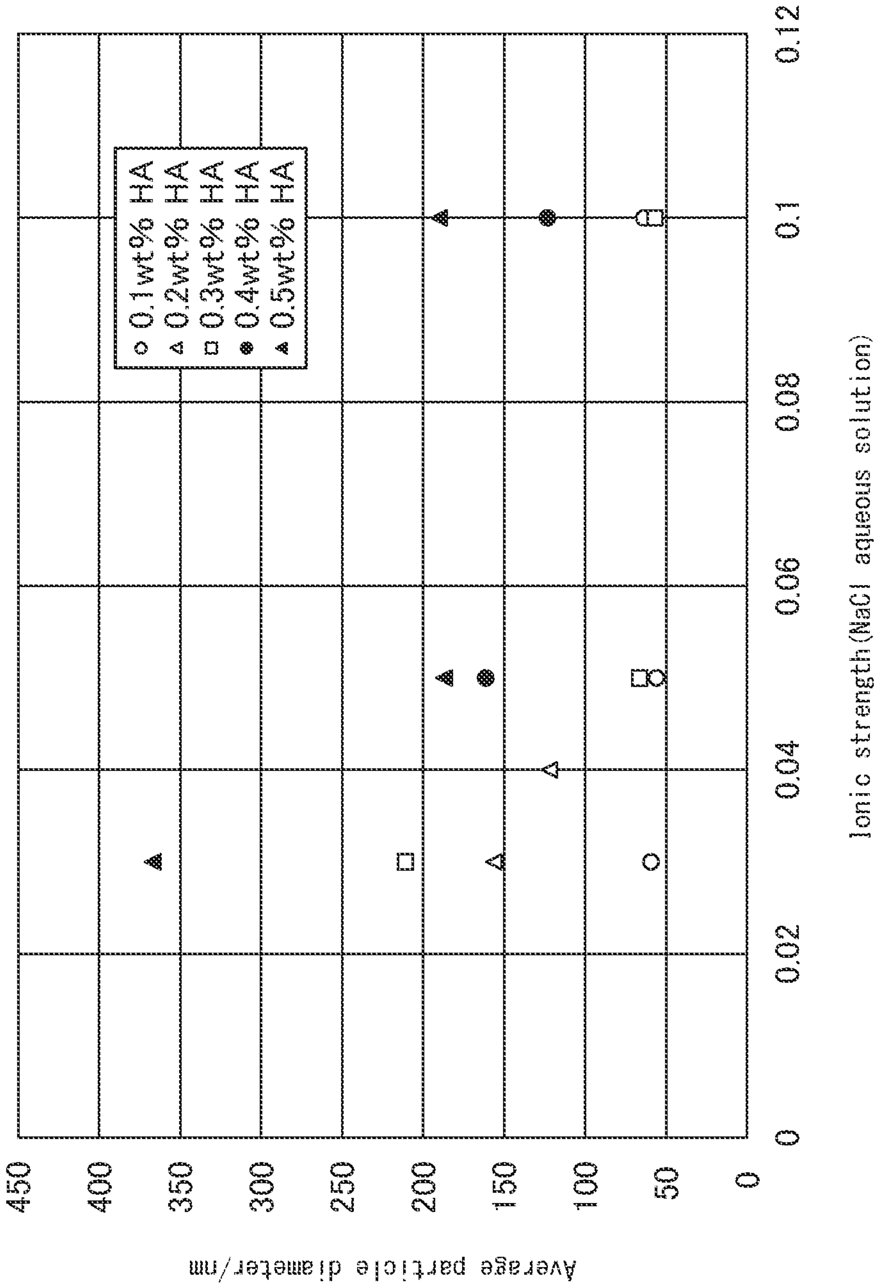
FIG. 6 is a graph related to the Z average particle diameter and the ionic strength of hyaluronic acid particles in each of compositions containing hyaluronic acid at various concentrations, which compositions were prepared using sodium chloride.

As is apparent from the results in Table 7 and FIG. 6, it was confirmed that, even at an increased concentration of hyaluronic acid, nanoscale hyaluronic acid particles can be obtained by adding a salt.

Reference Test Example 3: Effect of Ionic Strength at Hyaluronic Acid Concentration of 0.4 to 0.5% by Mass In Reference Test Example 3, the effect of the ionic strength on the hyaluronic acid particles was studied for cases where the concentration of hyaluronic acid at the time of preparation of the composition was 0.4 to 0.5% by mass. The results are shown in Table 8 and FIG. 7.

(Method for Preparing Compositions)

Hyaluronic acid particle-containing compositions were each prepared in the same manner as in Reference Test Example 1, except that the concentration of hyaluronic acid was 0.4% by mass or 0.5% by mass, and that sodium chloride was added such that the ionic strength was at the ratio described in Table 8.

TABLE 8

| | HA concentration | Ionic strength | | | | | | | |
|---|---|---|---|---|---|---|---|---|---|
| | (% by mass) | 0.03 | 0.05 | 0.10 | 0.20 | 0.50 | 1.0 | 2.0 | 4.0 |
| Average particle diameter (nm) | 0.4 | — | 161 | 123 | 84 | — | 90 | 130 | 175 |
| | 0.5 | 367 | 187 | 190 | 145 | 142 | 157 | 139 | 172 |

(Results)

Figure 7:
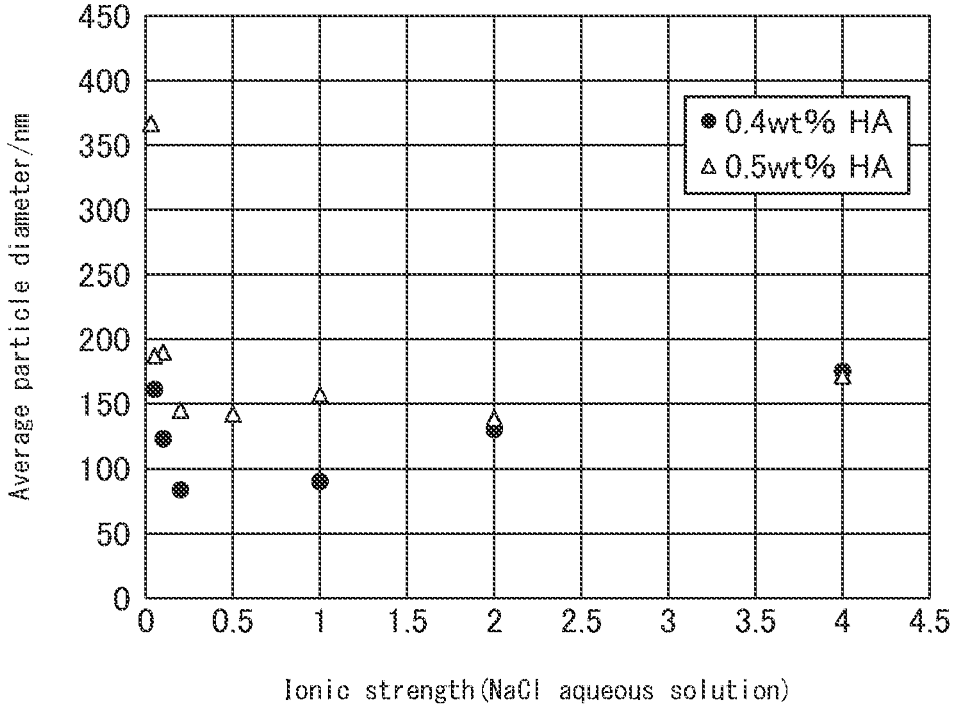
FIG. 7 is a graph related to the Z average particle diameter and the ionic strength of hyaluronic acid particles in each of compositions containing hyaluronic acid at a concentration of 0.4% by mass or 0.5% by mass, which compositions were prepared using sodium chloride.

As is apparent from the results in Table 8 and FIG. 7, it could be confirmed that, when the ionic strength was 0.05 or more, hyaluronic acid particles with a diameter of 200 nm or less can be obtained in both cases where the concentration of hyaluronic acid is 0.4% by mass or 0.5% by mass. In particular, it could be confirmed that, when the concentration of hyaluronic acid is 0.4% by mass, hyaluronic acid particles with a diameter of 100 nm or less can be obtained at an ionic strength within the range of 0.20 to 1.0.

Reference Test Example 4: Effect of Particle Diameter of Hyaluronic Acid Particles on Moisture-Retaining Property In Reference Test Example 4, the effect of the particle diameter of hyaluronic acid particles on the moisture-retaining property was studied. The results are shown in Table 9 and FIG. 8. Here, as the water content ratio exceeds 1 and increases further, the moisture-retaining performance can be said to be improved compared with that in the state before the application of the composition. The water content ratio is preferably 1.25 or more, more preferably 1.30 or more, particularly preferably 1.35 or more.

(Method for Preparing Compositions)

Hyaluronic acid particle-containing compositions were each prepared in the same manner as in Reference Test Example 1, except that the concentration of hyaluronic acid was 0.4% by mass, and that sodium chloride was added such that the ionic strength was at the ratio described in Table 9. Here, in the composition prepared without adding sodium chloride, that is, in the composition having an ionic strength of 0, hyaluronic acid molecules are thought to be in the form of spread filaments rather than in the form of particles. Such a state is thus denoted as “Non-particle” in the table and the figure.

TABLE 9

| HA concentration | Ionic | Average particle | Time (minutes) | | | | |
|---|---|---|---|---|---|---|---|
| 0.4% by mass | strength | diameter (nm) | 0 | 15 | 30 | 60 | 120 |
| Water content ratio | 0 | Non-particle | 1.00 | 1.17 | 1.13 | 1.17 | 1.16 |
| | 0.02 | 534 | 1.00 | 1.18 | 1.12 | 1.08 | 1.07 |
| | 0.03 | 294 | 1.00 | 1.21 | 1.13 | 1.14 | 1.13 |
| | 0.20 | 84 | 1.00 | 1.39 | 1.45 | 1.51 | 1.53 |

(Results)

Figure 8:
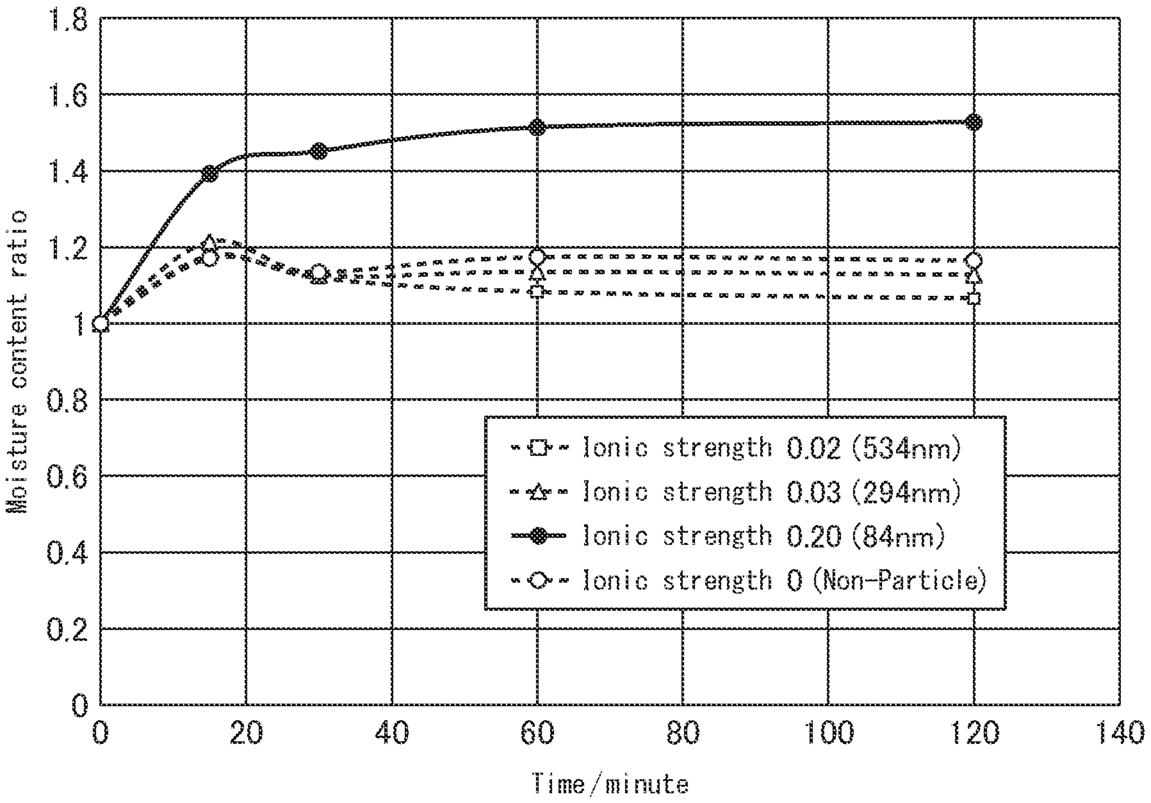
FIG. 8 is a graph related to the Z average particle diameter and the moisture-retaining performance of hyaluronic acid particles.

As is apparent from the results in Table 9 and FIG. 8, the composition containing non-particle hyaluronic acid, and the compositions containing hyaluronic acid particles having an average particle diameter of 294 nm or more, temporarily showed increases in the moisture-retaining performance immediately after the application of each composition to the skin. However, the moisture-retaining performance decreased in only about 30 minutes to almost the same level as in the case without application of the composition. This is thought to be due to the fact that the hyaluronic acid in these compositions did not penetrate into the skin.

On the other hand, it could be confirmed that, in the case of a composition containing hyaluronic acid particles having an average particle diameter of 84 nm, an excellent moisture-retaining performance can be produced from immediately after application of the composition to the skin, and that its moisture-retaining performance can be maintained over a long period of time. It is thought that the action effect involved in the immediate effect and the persistence of this moisture-retaining performance is derived from the fact that the hyaluronic acid particles are in the form of ultrafine particles of 200 nm or less, which easily penetrate into the skin, and that the content ratio of hyaluronic acid in the particles is high.

Reference Test Example 5: Effect of Sodium Citrate on Particle Diameter of Hyaluronic Acid Particles In Reference Test Example 5, the effect of sodium citrate on the particle diameter of hyaluronic acid particles was studied. The results are shown in Table 10 and FIG. 9.

(Method for Preparing Compositions)

Hyaluronic acid (manufactured by Shiseido Co., Ltd., Biohyaluro 12: weight average molecular weight 1.2 million) was added to a citrate buffer (manufactured by Fujifilm Wako Pure Chemical Co., Ltd.: pH 6.5, ionic strength 0.006) to a content of 0.1% by mass, and the resulting mixture was stirred and mixed by a vortex mixer, to prepare Composition C. After dissolving the hyaluronic acid, sodium citrate was added to aliquots of Composition C such that the ionic strength of the salt was 0.03, 0.06, or 0.30, and the mixture was stirred and mixed by a vortex mixer, to prepare each hyaluronic acid particle-containing composition. Here, the concentration of sodium citrate at an ionic strength of 0.03 was 0.005 M; the concentration of sodium citrate at an ionic strength of 0.06 was 0.010 M; and the concentration of sodium citrate at an ionic strength of 0.30 was 0.050 M.

TABLE 10

| HA concentration | Ionic strength | | | |
|---|---|---|---|---|
| 0.1% by mass | 0.006 | 0.03 | 0.06 | 0.30 |
| Average particle diameter (nm) | 6,100 | 51 | 60 | 86 |

(Results)

Figure 9:
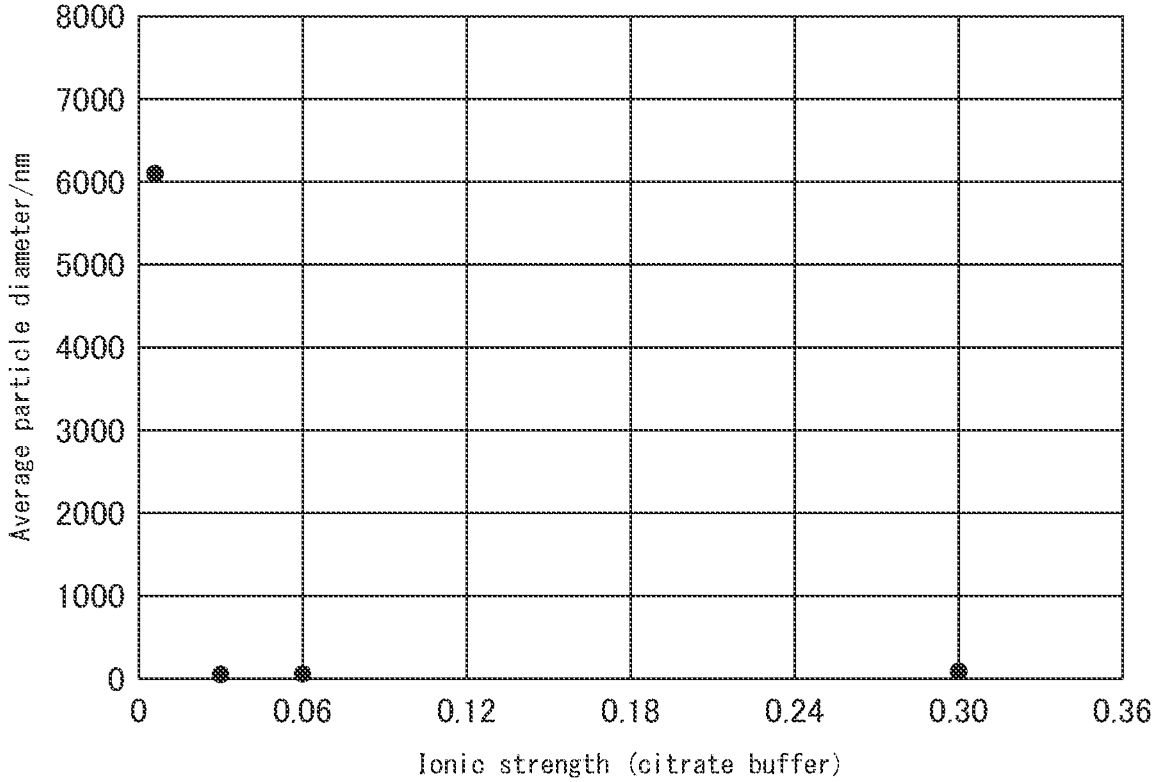
FIG. 9 is a graph related to the Z average particle diameter and the ionic strength of hyaluronic acid particles prepared using citrate buffer.

As is apparent from the results in Table 10 and FIG. 9, it could be confirmed that hyaluronic acid particles with a diameter of 200 nm or less can be obtained also with a salt other than sodium chloride.

Reference Test Example 6: Effect of Use of Additive That Inhibits Hydrogen Bonding, on Particle Diameter of Hyaluronic Acid Particles From Reference Test Example 6, a study was carried out to investigate the effect of use of urea as an additive that inhibits hydrogen bonding, on the particle diameter of hyaluronic acid particles. The results are shown in Table 11 and FIG. 10.

Reference Example 1

Hyaluronic acid (manufactured by Shiseido Co., Ltd., Biohyaluro 12: weight average molecular weight 1.2 million) was added to ion-exchanged water to a content of 0.1% by mass, and the mixture was stirred and mixed by a vortex mixer, to prepare Composition D. After dissolving the hyaluronic acid, sodium chloride was added at a concentration of 0.10 M to Composition D so that the ionic strength of the salt was 0.10, and the mixture was stirred and mixed by a vortex mixer, to prepare a hyaluronic acid particle-containing composition.

Reference Example 2

Hyaluronic acid (manufactured by Shiseido Co., Ltd., Biohyaluro 12: weight average molecular weight 1.2 million) was added to an isotonic phosphate buffer (manufactured by Takara Bio Inc.: pH 7.4, ionic strength 0.154) to a content of 0.1% by mass, and the resulting mixture was stirred and mixed by a vortex mixer, to prepare a hyaluronic acid particle-containing composition.

Reference Comparative Example 1

The composition of Reference Comparative Example 1 was prepared by including urea at 10% by mass with respect to the total amount of the hyaluronic acid particle-containing composition of Reference Example 1.

Reference Comparative Example 2

The composition of Reference Comparative Example 2 was prepared by including urea at 10% by mass with respect to the total amount of the hyaluronic acid particle-containing composition of Reference Example 2.

TABLE 11

| | Reference Example 1 | Reference Example 2 | Reference Comparative Example 1 | Reference Comparative Example 2 |
|---|---|---|---|---|
| Average particle diameter (nm) | 83 | 80 | 320 | 314 |

(Results)

From the results in Table 11 and FIG. 10, it could be confirmed that a remarkable increase in the particle diameter of the hyaluronic acid particles occurs when urea, which has an action to break hydrogen bonds, is added to the composition. As is apparent from this result, the hyaluronic acid particles prepared using a salt showed changes in the particle diameter due to the inclusion of urea, which breaks hydrogen bonds. It is thus thought that the hyaluronic acid particles are particles formed by hydrogen bonding, rather than particles that are obtained by cross-linking and not affected by urea.

The invention claimed is:

1. A cosmetic comprising:

a first agent configured for application to and spreading on a body surface or body hair, containing:

at least one salt selected from the group consisting of an inorganic salt and an organic acid salt;

hyaluronic acid; and an aqueous medium;

a second agent for swelling the hyaluronic acid, the second agent containing:

a chelating agent, wherein the organic acid salt is at least one selected from the group consisting of citrate, acetate, lactate, tartrate, succinate, malate, glycolate, salicylate, and pyrrolidone carboxylate, wherein the hyaluronic acid is compacted by the salt to form a particle having an average particle diameter of 200 nm or less at a sufficient ionic strength, and wherein the volume of the compacted hyaluronic acid in the first agent increases continuously by application of the second agent to the first agent.

2. The cosmetic according to claim 1, wherein the hyaluronic acid is contained at 0.005% by mass or more with respect to the total amount of the first agent.

3. The cosmetic according to claim 1, wherein the salt comprises a cation, and the cation wherein is a metal ion.

4. The cosmetic according to claim 1, wherein the chelating agent is at least one selected from the group consisting of ethylenediaminetetraacetic acid, disodium ethylenediaminetetraacetate, trisodium ethylenediaminetetraacetate, nitrilotriacetic acid, sodium nitrilotriacetate, ammonium nitrilotriacetate, hydroxyethylethylenediaminetriacetic acid, sodium hydroxyethylethylenediaminetriacetate, pentetic acid, pentasodium pentetate, triethylenetetramine hexaacetic acid, sodium triethylenetetramine hexaacetate, imidisuccinic acid, tetrasodium imidisuccinate, ethylenediaminedisuccinic acid, trisodium ethylenediamine disuccinate, hydroxyethyliminodiacetic acid, disodium hydroxyethyliminodiacetate, iminodisuccinic acid, tetrasodium iminodisuccinate, methylglycine diacetic acid, trisodium methylglycine diacetate, hydroxyiminodisuccinic acid, tetrasodium hydroxyiminodisuccinate, L-aspartic acid diacetic acid, tetrasodium L-aspartate diacetate, glutamic acid diacetic acid, tetrasodium glutamate diacetate, propanediaminetetraacetic acid, diammonium ethylenediaminetetraacetate, 1,3-diamino-2-hydroxypropane-tetraacetic acid, N,N-bis(2-hydroxyethyl)glycine, glycol ether diamine tetraacetic acid, dicarboxymethyl glutamic acid, tetrasodium dicarboxymethyl glutamate, hexametaphosphoric acid, diethylenetriaminepentaacetic acid, sodium hexametaphosphate, nitrilotris(methylenephosphonic acid), potassium nitrilotris (methylenephosphonate), 2-phosphonobutane-1,2,4-tricarboxylic acid, ethylenediaminetetramethylene phosphonic acid, pentasodium ethylenediaminetetramethylene phosphonate, phytic acid, and citric acid.

5. The cosmetic according to claim 1, wherein the weight average molecular weight of the hyaluronic acid is 10,000,000 or less.

6. A cosmetic method using the cosmetic according to claim 1, the method comprising:

applying the first agent to a body surface or body hair; and then applying the second agent to the application area of the first agent.

7. The cosmetic according to claim 1, wherein the salt is contained at 0.10% by mass or more and 5.0% by mass or less with respect to the total amount of the first agent.

* * * * *